US010640739B2

(12) United States Patent
Shan et al.

(10) Patent No.: US 10,640,739 B2
(45) Date of Patent: May 5, 2020

(54) **BACTERICIDAL, FUNGICIDAL AND ANTI-ALLERGENIC *ZANTHOXYLUM SCHINIFOLIUM* SKIN CARE SOAP AND METHOD OF PREPARATION**

(71) Applicants: NANJING INST OF COMPREH UTILIZATION OF WILD PLANTS, Nanjing (CN); DONGPING JIUXIN BIO-CHEMISTRY CO., LTD., Taian (CN)

(72) Inventors: Chengying Shan, Nanjing (CN); Weiming Zhang, Nanjing (CN); Shihong Ma, Nanjing (CN); Guoqing Chen, Taian (CN); Haibo Wang, Taian (CN); Shuhong Li, Taian (CN)

(73) Assignees: NANJING INST OF COMPREH UTILIZATION OF WILD PLANTS, Nanjing (CN); DONGPING JIUXIN BIO-CHEMISTRY CO., LTD., Taian (CN)

( * ) Notice: Subject to any disclaimer, the term of this patent is extended or adjusted under 35 U.S.C. 154(b) by 242 days.

(21) Appl. No.: 15/399,499

(22) Filed: Jan. 5, 2017

(65) Prior Publication Data

US 2017/0191010 A1 Jul. 6, 2017

(30) Foreign Application Priority Data

Jan. 6, 2016 (CN) .......................... 2016 1 0006513

(51) Int. Cl.

| | |
|---|---|
| ***A61K 36/00*** | (2006.01) |
| ***A61K 36/75*** | (2006.01) |
| ***C11D 17/00*** | (2006.01) |
| ***C11D 3/20*** | (2006.01) |
| ***C11D 3/382*** | (2006.01) |
| ***C11D 3/48*** | (2006.01) |
| ***C11D 9/08*** | (2006.01) |
| ***C11D 9/26*** | (2006.01) |
| ***C11D 9/38*** | (2006.01) |
| ***C11D 10/04*** | (2006.01) |
| ***C11D 13/10*** | (2006.01) |
| ***C11D 13/12*** | (2006.01) |
| ***C11D 13/16*** | (2006.01) |

(52) U.S. Cl.

CPC ........ *C11D 17/0047* (2013.01); *C11D 3/2044* (2013.01); *C11D 3/2065* (2013.01); *C11D 3/382* (2013.01); *C11D 3/48* (2013.01); *C11D 9/08* (2013.01); *C11D 9/26* (2013.01); *C11D 9/265* (2013.01); *C11D 9/267* (2013.01); *C11D 9/38* (2013.01); *C11D 10/042* (2013.01); *C11D 13/10* (2013.01); *C11D 13/12* (2013.01); *C11D 13/16* (2013.01); *C11D 17/006* (2013.01)

(58) Field of Classification Search

None

See application file for complete search history.

(56) References Cited

FOREIGN PATENT DOCUMENTS

| | | | | |
|---|---|---|---|---|
| CN | 101623246 | A | * | 1/2010 |
| CN | 103655225 | A | * | 3/2014 |
| CN | 104042512 | A | * | 9/2014 |
| CN | 104306211 | A | * | 1/2015 |
| KR | 2009080827 | A | * | 2/2009 |
| KR | 1002012 | B1 | * | 12/2010 |
| WO | WO2015180697 | A1 | * | 12/2015 |

* cited by examiner

*Primary Examiner* — Michael Barker
*Assistant Examiner* — Randall Winston
(74) *Attorney, Agent, or Firm* — Troutman Sanders LLP; Christopher C. Close, Jr.

(57) ABSTRACT

The present invention discloses a method of preparing a bactericidal, fungicidal and anti-allergenic *Zanthoxylum schinifolium* skin care soap, wherein the bactericidal, fungicidal and anti-allergenic *Zanthoxylum schinifolium* skin care soap comprises the following components based on percentage by weight: Component A: *Zanthoxylum schinifolium* seed oil 15.0-21.0%, propylene glycol 12.0-17.0%, glycerin 6.0-11.0%, Component B: deionized water 5.0-8.0%, sodium alkyl ether sulfate AES 8.0-12.0%, Component C: lauric acid 5.0-8.0%, stearic acid 11.0-16.0%, Component D: 98% NaOH 2.5-4.5%, deionized water balance, Component E: *Zanthoxylum schinifolium* essential oil 0.3-0.8%. The skin care soap of the present invention is pale yellow and translucent, has good stability, provides great aroma and rich foam, and can nourish the skin and sterilize effectively.

5 Claims, No Drawings

BACTERICIDAL, FUNGICIDAL AND ANTI-ALLERGENIC *ZANTHOXYLUM SCHINIFOLIUM* SKIN CARE SOAP AND METHOD OF PREPARATION

TECHNICAL FIELD

This invention is related to a detergent cleaning product, especially a bactericidal, fungicidal and anti-allergenic *Zanthoxylum schinifolium* skin care soap and its method of preparation.

BACKGROUND

Consumers are very familiar with soap products for cleaning in daily life. Depending on the applications, soap products can be divided into two categories: detergents mainly for cleaning cloth, and detergents mainly for cleaning human skin. The facial, hand and body soaps include, but are not limited to skin care soaps. Different consumers have different needs for performance of soap products. With respect to cleaning skin, the skin feeling after cleaning is as important as cleaning power. Currently, almost all of the bactericidal, fungicidal hand soaps, facial cleansers, and body wash soaps on the market contain synthetic bactericidal and/or fungicidal agents as the main bactericidal and/or fungicidal components. Consumers sometimes experience allergic reactions, such as dry skin, itching, stinging, etc. after using these products. Therefore, there is a great need in the field to develop abactericidal, fungicidal skin care soap containing a natural bactericidal or fungicidal component that will not cause skin allergic reaction.

*Zanthoxylum schinifolium* is an economic plant that grows only in China. It is a species in the Rutaceae family as *Zanthoxylum bungeanum Maxim* that is a commonly used spice. However, *Zanthoxylum schinifolium* and *Zanthoxylum bungeanum Maxim* are different species in the Rutaceae family. *Zanthoxylum schinifolium* is also an important spice and an important ingredient in Chinese medicine. The shells of *Zanthoxylum schinifolium* seeds contain rich content of volatile essential oil. The major components in the essential oil are linalool, D-lemonene and terpene alcohol, etc. *Zanthoxylum schinifolium* essential oil has an excellent bactericidal effect. Based on the presently available research results, *Zanthoxylum schinifolium* essential oils extracted by various methods inhibit *Staphylococcus aureus, Candida tropicalis, Candida albicans*, White ground bacteria, *Aspergillus fumigatus*, and *Aspergillus niger* at varying degrees.

*Zanthoxylum schinifolium* nut oil is an edible vegetable oil, which can be extracted from the nuts of *Zanthoxylum schinifolium* seeds by modern oil production processes. *Zanthoxylum schinifolium* nut oil contains rich content of unsaturated fatty acids, in which $\alpha$-linolenic acid content is up to above 33.0%. Unsaturated fatty acids are essential to the human body. With respect to $\alpha$-linolenic acid, it is also called "brain gold." In addition to its health benefits, when added into consumer goods, $\alpha$-linolenic acid has an excellent fungicidal effect.

Under the present spice processing practices, *Zanthoxylum schinifolium* seeds are either used for extracting *Zanthoxylum schinifolium* essential oil only, and the edible oil in the nuts are discarded; or *Zanthoxylum schinifolium* seeds are shelled and crushed for extracting *Zanthoxylum schinifolium* essential oil. The crushed shells contain rich content of essential oil but are discarded. Both practices cause a huge waste of resources. Therefore, the question as to how to make the best use the oils in *Zanthoxylum schinifolium* seeds is an important one for processing *Zanthoxylum schinifolium* seeds.

Currently, a bactericidal, fungicidal and anti-allergenic *Zanthoxylum schinifoliu* skin care soap and method of preparation are lacking.

SUMMARY OF THE DISCLOSURE

The present invention is directed to a bactericidal, fungicidal and anti-allergenic *Zanthoxylum schinifoliu* skin care soap and method of preparation in light of the above noted current technical deficiencies.

The objectives of the present invention can be achieved by the technical solutions provided below: The present invention provides a bactericidal, fungicidal and anti-allergenic *Zanthoxylum schinifolium* skin care soap, wherein the bactericidal, fungicidal and anti-allergenic *Zanthoxylum schinifolium* skin care soap comprises the following components based on weight percentage:

| | | |
|---|---|---|
| Component A: | *Zanthoxylum schinifolium* nut oil | 15.0-21.0%, |
| | Propylene glycol | 12.0-17.0%, |
| | Glycerin | 6.0-11.0%, |
| Component B: | Deionized water | 5.0-8.0%, |
| | Sodium alkyl ether sulfate AES | 8.0-12.0%, |
| Component C: | Lauric acid | 5.0-8.0%, |
| | Stearic acid | 11.0-16.0%, |
| Component D: | 98% NaOH | 2.5-4.5%, |
| | Deionized water | balance, |
| Component E: | *Zanthoxylum schinifolium* essential oil | 0.3-0.8%. |

Furthermore, the bactericidal, fungicidal and anti-allergenic *Zanthoxylum schinifolium* skin care soap comprises the following components based on weight percentage:

| | | |
|---|---|---|
| Component A: | *Zanthoxylum schinifolium* nut oil | 16.0-20.0%, |
| | Propylene glycol | 13.0-16.0%, |
| | Glycerin | 7.0-10.0%, |
| Component B: | Deionized water | 6.0-8.0%, |
| | Sodium alkyl ether sulfate AES | 9.0-12.0%, |
| Component C: | Lauric acid | 6.0-8.0%, |
| | Stearic acid | 12.0-15.0%, |
| Component D: | 98% NaOH | 2.5-4.0%, |
| | Deionized water | balance, |
| Component E: | *Zanthoxylum schinifolium* essential oil | 0.3-0.6%. |

The present invention provides a method of preparing a bactericidal, fungicidal and anti-allergenic *Zanthoxylum schinifolium* skin care soap, which comprises the following steps:

(1) add *Zanthoxylum schinifolium* nut oil, propylene glycol, and glycerin of Component A into an emulsifying pot, start agitation, and raise temperature to 50-62° C., and dissolve Component A homogeneously;

(2) add deionized water and sodium alkyl ether sulfate AES of Component B into the emulsifying pot, mix homogeneously, and maintain temperature at 50-62° C.;

(3) add lauric acid and stearic acid of Component C into the emulsifying pot to melt, maintain temperature at 50-62° C.;

(4) dissolve 98% NaOH in water of Component D, and maintain temperature at 50-62° C.;

(5) add Component D into the emulsifying pot, agitate, and control the temperature of the materials at 75-85° C.;

(6) add *Zanthoxylum schinifolium* essential oil of Component E into the emulsifying pot, and control the temperature of the materials at 75-85° C.;

(7) defoam under vacuum for 15-25 minutes; confirm the semi-finished product, pour the materials from the emulsifying pot into a mold, and obtain said bactericidal, fungicidal and anti-allergenic *Zanthoxylum schinifolium* skin care soap after cooling.

Furthermore, in step (1) the *Zanthoxylum schinifolium* nut oil contains 82.0-92.0% of total unsaturated fatty acids based on weight percentage, and the total unsaturated fatty acids contain 28.0-33.0% of α-linolenic acid based on weight percentage.

Furthermore, step (1) comprises collecting and drying *Zanthoxylum schinifolium* seeds that have been extracted for essential oil, placing them in a Soxhlet extractor for extraction, heat refluxing for 3-5 hours using petroleum ether as solvent, wherein the petroleum ether has a boiling point range of 30-60° C., recovering petroleum ether after extraction by heat, and obtaining the *Zanthoxylum schinifolium* nut oil.

Furthermore, in step (6) the *Zanthoxylum schinifolium* essential oil comprises the following components based on weight percentage:

| | |
|---|---|
| Linalool | 58.0-65.0%, |
| D-lemonene | 3.5-6.5%, |
| 4-methyl-1-isopropyl-3-cyclohexene-1-ol (terpene alcohol) | 2.5-5.5%. |

Furthermore, in step (6), the *Zanthoxylum schinifolium* essential oil is prepared by: crushing *Zanthoxylum schinifolium* seeds under room temperature, passing through a 10 mesh sieve, adding water, and steam distilling assisted by microwaves, wherein the weight ratio of *Zanthoxylum schinifolium* seeds to water is 1:3-8; the microwave power is set at 150-350 W, and the microwave-assisted extraction time is 1.5-3 hours.

Furthermore, in step (5) the saponification time is 15-25 minutes.

Furthermore, the pH value of the bactericidal, fungicidal and anti-allergenic *Zanthoxylum schinifolium* skin care soap is 7.5-10.0.

Beneficial effects: the *Zanthoxylum schinifolium* skin care soap of the present invention is pale yellow and translucent, has good stability, provides great aroma and rich foam, and can nourish skin and sterilize effectively; the present skin care soap contains fungicidal ingredients, which can effectively slow down skin allergic reaction, and keep skin clean, smooth and moist. The oil extracted from *Zanthoxylum schinifolium* nuts contain a rich content of unsaturated fatty acids, which can effectively improve skin sensitivity after cleaning, and can greatly enhance moist feeling of skin.

When compared with the existing technology, the present invention has the following advantages:

(1) Both *Zanthoxylum schinifolium* essential oil and nut oil are fully extracted from *Zanthoxylum schinifolium* seeds, and the present invention uses both oils, i.e., *Zanthoxylum schinifolium* essential oil and *Zanthoxylum schinifolium* nut oil as the main active ingredients for bactericidal and fungicidal effect. The beneficial effects of the present invention are from *Zanthoxylum schinifolium*, the volatile essential oil extracted from shells of *Zanthoxylum schinifolium* seeds, and the edible nut oil extracted from *Zanthoxylum schinifolium* nuts, respectively. *Zanthoxylum schinifolium* nut oil contains a rich content of unsaturated fatty acids, which is beneficial for skin growth, and is known as an anti-allergenic ingredient; and the rich content of fatty acids plays an important role in preparing the soap of the present invention, it provides sufficient foaming, cleaning power and moist skin feeling. In traditional soap compositions and soap making, palm oil, coconut oil or combination of palm and coconut oils are typically used as vegetable oils. However, these two types of oils mainly contain saturated fatty acids, and the skin feeling is poor after using soaps containing them, and may cause dry skin, itchiness and other allergic reactions especially in consumers who have sensitive skin.

(2) *Zanthoxylum schinifolium* essential oil is a natural oil having a sterilization effect. The present inventors researched different extraction methodologies (steam distillation, solvent extraction, carbon dioxide supercritical fluid extraction) and tested their bactericidal effect. The results have shown that *Zanthoxylum schinifolium* essential oil extracted by different methods vary slightly in their bactericidal and fungicidal effects. Among the *Zanthoxylum schinifolium* essential oil extracted by different methods, *Zanthoxylum schinifolium* essential oil extracted from steam distillation showed the highest bactericidal and fungicidal effect, it can effectively kill various bacteria and fungi, such as *Staphylococcus aureus, Candida albicans, Escherichia coli*, and *Pseudomoas aeruginosa*. Therefore, the present invention uses *Zanthoxylum schinifolium* essential oil prepared by steam distillation. Steam distillation guarantees that the materials after essential oil extraction can be further used to extract *Zanthoxylum schinifolium* nut oil. Skin care soap containing *Zanthoxylum schinifolium* essential oil as the major bactericidal and fungicidal ingredient avoids the use of chemical bactericidal and/or fungicidal agent, such as triclosan, which causes poor skin feeling and poses a potential carcinogenic risk, etc.

DETAILED DISCLOSURE

The present invention is further described by the following examples. However, the examples are provided for the purpose of illustration and are not to be construed as limitations of the scope of the invention in any form.

Example 1

Preparation of *Zanthoxylum schinifolium* Essential Oil

Take 100 grams of *Zanthoxylum schinifolium* seeds, crush under room temperature, sieve through a 10-mesh screen, and place them in an essential oil extraction equipment, and then add water. The weight ratio between seeds to water is 1:3. Set microwave power at 150 W, extract assisted by microwaves for 1.5 hours; under these conditions, the yield of essential oil is 7.8%. The extracted essential oil is pale yellow and transparent, and has a rich and characteristic *Zanthoxylum schinifolium* fragrance.

*Zanthoxylum schinifolium* essential oil obtained above has the following components based on weight percentage:

| | |
|---|---|
| Linalool | 58.0%, |
| D-lemonene | 3.5%, |
| 4-methyl-1-isopropyl-3-cyclohexene-1-ol (terpene alcohol) | 2.5%. |

Preparation of *Zanthoxylum schinifolium* Nut Oil

Collect and dry *Zanthoxylum schinifolium* seeds that have been extracted for essential oil, place them in a Soxhlet extractor for extraction using petroleum ether (30-60° C.) as solvent, heat to reflux, and reflux for 3 hours under a micro-boiling state, recover petroleum ether after extraction by heat to obtain *Zanthoxylum schinifolium* nut oil. Under these conditions, the yield of nut oil is 21.6%. The extracted nut oil is pale yellow and transparent, and has a rich fragrance.

*Zanthoxylum schinifolium* nut oil obtained above contains 82.0% of total unsaturated fatty acids based on weight percentage, and the total unsaturated fatty acids contain 28.0% of α-linolenic acid based on weight percentage.

The bactericidal, fungicidal and anti-allergenic *Zanthoxylum schinifolium* skin care soap of the present invention comprises the following components based on weight percentage:

| | | |
|---|---|---|
| Component A: | *Zanthoxylum schinifolium* nut oil | 15.0%, |
| | Propylene glycol | 12.0%, |
| | Glycerin | 6.0%, |
| Component B: | Deionized water | 5.0%, |
| | Sodium alkyl ether sulfate AES | 8.0%, |
| Component C: | Lauric acid | 5.0%, |
| | Stearic acid | 11.0%, |
| Component D: | 98% NaOH | 2.5%, |
| | Deionized water | balance, |
| Component E: | *Zanthoxylum schinifolium* essential oil | 0.3%. |

The method of preparing the bactericidal, fungicidal and anti-allergenic *Zanthoxylum schinifolium* skin care soap of the present invention comprises the following steps:

(1) add Component A into an emulsifying pot, start agitation, and raise temperature to 50° C., confirm that Component A dissolves homogeneously;

(2) add Component B, mix homogeneously, and maintain temperature at 50° C.;

(3) add Component C and melt Component C, and maintain temperature at 50° C.;

(4) dissolve Component D, and maintain temperature at 50° C.;

(5) add Component D, agitate, saponify for 15 minutes, and control the temperature of materials at 75° C.;

(6) add Component E, agitate for 10 minutes, and control the temperature of the materials at 75° C.;

(7) defoam under vacuum for 15 minutes; confirm the semi-finished product, pour the materials from the emulsifying pot into a mold, and obtain the bactericidal, fungicidal and anti-allergenic *Zanthoxylum schinifolium* skin care soap after cooling.

The bactericidal, fungicidal and anti-allergenic *Zanthoxylum schinifolium* skin care soap has a pH of 8.0.

Example 2

Example 2 differs from Example 1 in that:

Take 100 grams of *Zanthoxylum schinifolium* seeds, crush under room temperature, sieve through a 10-mesh screen, and place them in an essential oil extraction equipment, and then add water. The weight ratio between seeds to water is 1:5. Set microwave power at 250 W, extract assisted by microwaves for 2 hours; under these conditions, the yield of essential oil is 8.2%. The extracted essential oil is pale yellow and transparent, and has a rich and characteristic *Zanthoxylum schinifolium* fragrance.

*Zanthoxylum schinifolium* essential oil obtained above has the following components based on weight percentage:

| | |
|---|---|
| Linalool | 60.0%, |
| D-lemonene | 4.5%, |
| 4-methyl-1-isopropyl-3-cyclohexene-1-ol (terpene alcohol) | 3.5%. |

Preparation of *Zanthoxylum schinifolium* Nut Oil

Collect and dry *Zanthoxylum schinifolium* seeds that have been extracted for essential oil, place them in a Soxhlet extractor for extraction using petroleum ether (30-60° C.) as solvent, heat to reflux, and reflux for 3.5 hours under a micro-boiling state, recover petroleum ether after extraction by heat to obtain *Zanthoxylum schinifolium* nut oil. Under these conditions, the yield of nut oil is 21.9%. The extracted nut oil is pale yellow and transparent, and has a rich fragrance.

*Zanthoxylum schinifolium* nut oil obtained above contains 85.0% of total unsaturated fatty acids based on weight percentage, and the total unsaturated fatty acids contain 30.0% of α-linolenic acid based on weight percentage.

The bactericidal, fungicidal and anti-allergenic *Zanthoxylum schinifolium* skin care soap of the present invention comprises the following components based on weight percentage:

| | | |
|---|---|---|
| Component A: | *Zanthoxylum schinifolium* nut oil | 17.0%, |
| | Propylene glycol | 13.5%, |
| | Glycerin | 7.5%, |
| Component B: | Deionized water | 6.0%, |
| | Sodium alkyl ether sulfate AES | 9.5%, |
| Component C: | Lauric acid | 6.0%, |
| | Stearic acid | 12.5%, |
| Component D: | 98% NaOH | 3.0%, |
| | Deionized water | balance, |
| Component E: | *Zanthoxylum schinifolium* essential oil | 0.45%. |

The method of preparing the bactericidal, fungicidal and anti-allergenic *Zanthoxylum schinifolium* skin care soap of the present invention comprises the following steps:

(1) add Component A into an emulsifying pot, start agitation, and raise temperature to 55° C., confirm that Component A dissolves homogeneously;

(2) add Component B, mix homogeneously, and maintain temperature at 55° C.;

(3) add Component C and melt Component C, and maintain temperature at 55° C.;

(4) dissolve Component D, and maintain temperature at 55° C.;

(5) add Component D, agitate, saponify for 18 minutes, and control the temperature of materials at 78° C.;

(6) add Component E, agitate for 10 minutes, and control the temperature of the materials at 78° C.;

(7) defoam under vacuum for 18 minutes; confirm the semi-finished product, pour the materials from the emulsifying pot into a mold, and obtain the bactericidal, fungicidal and anti-allergenic *Zanthoxylum schinifolium* skin care soap after cooling.

The bactericidal, fungicidal and anti-allergenic *Zanthoxylum schinifolium* skin care soap has a pH of 8.5.

Example 3

Example 3 differs from Example 1 in that:

Take 100 grams of *Zanthoxylum schinifolium* seeds, crush under room temperature, sieve through a 10-mesh screen, and place them in an essential oil extraction equipment, and add then water. The weight ratio between seeds to water is 1:6. Set microwave power at 300 W, extract assisted by microwaves for 2.5 hours; under these conditions, the yield of essential oil is 8.6%. The extracted essential oil is pale yellow and transparent, and has a rich and characteristic *Zanthoxylum schinifolium* fragrance.

*Zanthoxylum schinifolium* essential oil obtained above has the following components based on weight percentage:

| | |
|---|---|
| Linalool | 62.0%, |
| D-lemonene | 5.5%, |
| 4-methyl-1-isopropyl-3-cyclohexene-1-ol (terpene alcohol) | 4.5%. |

Preparation of *Zanthoxylum schinifolium* Nut Oil

Collect and dry *Zanthoxylum schinifolium* seeds that have been extracted for essential oil, place them in a Soxhlet extractor for extraction using petroleum ether (30-60° C.) as solvent, heat to reflux, and reflux for 4 hours under micro-boiling state, recover petroleum ether after extraction by heat to obtain *Zanthoxylum schinifolium* nut oil. Under these conditions, the yield of nut oil is 22.3%. The extracted nut oil is pale yellow and transparent, and has a rich fragrance.

*Zanthoxylum schinifolium* nut oil obtained above contains 88.0% of total unsaturated fatty acids based on weight percentage, and the total unsaturated fatty acids contain 31.0% of α-linolenic acid based on weight percentage.

The bactericidal, fungicidal and anti-allergenic *Zanthoxylum schinifolium* skin care soap of the present invention comprises the following components based on weight percentage:

| | | |
|---|---|---|
| Component A: | *Zanthoxylum schinifolium* nut oil | 19.0%, |
| | Propylene glycol | 15.5%, |
| | Glycerin | 9.0%, |
| Component B: | Deionized water | 7.0%, |
| | Sodium alkyl ether sulfate AES | 10.5%, |
| Component C: | Lauric acid | 7.0%, |
| | Stearic acid | 14.0%, |
| Component D: | 98% NaOH | 4.0%, |
| | Deionized water | balance, |
| Component E: | *Zanthoxylum schinifolium* essential oil | 0.6%. |

The method of preparing the bactericidal, fungicidal and anti-allergenic *Zanthoxylum schinifolium* skin care soap of the present invention comprises the following steps:

(1) add *Zanthoxylum schinifolium* nut oil, propylene glycol, and glycerin of Component A into an emulsifying pot, start agitation, raise temperature to 58° C., and dissolve Component A homogeneously;

(2) add deionized water and sodium alkyl ether sulfate AES of Component B, mix homogeneously, and maintain temperature at 58° C.;

(3) add lauric acid and stearic acid of Component C into the emulsifying pot to melt, and maintain temperature at 58° C.;

(4) dissolve 98% NaOH in water of Component D, and maintain temperature at 58° C.;

(5) add Component D, agitate, saponify for 22 minutes, and control the temperature of materials at 82° C.;

(6) add *Zanthoxylum schinifolium* essential oil of Component E, agitate for 10 minutes, and control the temperature of the materials at 82° C.;

(7) defoam under vacuum for 22 minutes; confirm the semi-finished product, pour the materials from the emulsifying pot into a mold, and obtain the bactericidal, fungicidal and anti-allergenic *Zanthoxylum schinifolium* skin care soap after cooling.

The bactericidal, fungicidal and anti-allergenic *Zanthoxylum schinifolium* skin care soap has a pH of 9.0

Example 4

Example 4 differs from Example 1 in that:

Take 100 grams of *Zanthoxylum schinifolium* seeds, crush under room temperature, sieve through a 10-mesh screen, and place them in an essential oil extraction equipment, and add water. The weight ratio between seeds to water is 1:8. Set microwave power at 350 W, extract assisted by microwaves for 3 hours; under these conditions, the yield of essential oil is 8.9%. The extracted essential oil is pale yellow and transparent, and has a rich and characteristic *Zanthoxylum schinifolium fragrance.*

*Zanthoxylum schinifolium* essential oil obtained above has the following components based on weight percentage:

| | |
|---|---|
| Linalool | 65.0%, |
| D-lemonene | 6.5%, |
| 4-methyl-1-isopropyl-3-cyclohexene-1-ol (terpene alcohol) | 5.5%. |

Preparation of *Zanthoxylum schinifolium* Nut Oil

Collect and dry *Zanthoxylum schinifolium* seeds that have been extracted for essential oil, place them in a Soxhlet extractor for extraction using petroleum ether (30-60° C.) as solvent, heat to reflux, and reflux for 5 hours under micro-boiling state, recover petroleum ether after extraction by heat to obtain *Zanthoxylum schinifolium* nut oil. Under these conditions, the yield of nut oil is 22.7%. The extracted nut oil is pale yellow and transparent, and has a rich fragrance.

*Zanthoxylum schinifolium* nut oil obtained above contains 92.0% of total unsaturated fatty acids based on weight percentage, and the total unsaturated fatty acids contain 33.0% of α-linolenic acid based on weight percentage.

The bactericidal, fungicidal and anti-allergenic *Zanthoxylum schinifolium* skin care soap of the present invention comprises the following components based on weight percentage:

| | | |
|---|---|---|
| Component A: | *Zanthoxylum schinifolium* nut oil | 21.0%, |
| | Propylene glycol | 17.0%, |
| | Glycerin | 11.0%, |
| Component B: | Deionized water | 8.0%, |
| | Sodium alkyl ether sulfate AES | 12.0%, |
| Component C: | Lauric acid | 8.0%, |
| | Stearic acid | 16.0%, |
| Component D: | 98% NaOH | 4.5%, |
| | Deionized water | balance, |
| Component E: | *Zanthoxylum schinifolium* essential oil | 0.8%. |

The method of preparing the bactericidal, fungicidal and anti-allergenic *Zanthoxylum schinifolium* skin care soap of the present invention comprises the following steps:

(1) add *Zanthoxylum schinifolium* nut oil, propylene glycol, and glycerin of Component A into an emulsifying pot, start agitation, raise temperature to 62° C., and dissolve Component A homogeneously;

(2) add deionized water and sodium alkyl ether sulfate AES of Component B, mix homogeneously, and maintain temperature at 62° C.;

(3) add lauric acid and stearic acid of Component C into the emulsifying pot to melt, and maintain temperature at 62° C.;

(4) dissolve 98% NaOH in water of Component D, and maintain temperature at 62° C.;

(5) add Component D, agitate, saponify for 25 minutes, and control the temperature of the materials at 85° C.;

(6) add *Zanthoxylum schinifolium* essential oil of Component E, agitate for 10 minutes, and control the temperature of the materials at 85° C.;

(7) defoam under vacuum for 25 minutes; confirm the semi-finished product, pour the materials from the emulsifying pot into a mold, and obtain the bactericidal, fungicidal and anti-allergenic *Zanthoxylum schinifolium* skin care soap after cooling.

The bactericidal, fungicidal and anti-allergenic *Zanthoxylum schinifolium* skin care soap has a pH of 9.5

Experiment 1

The bactericidal, fungicidal and anti-allergenic *Zanthoxylum schinifolium* skin care soaps prepared in Example 1 to Example 4 have the following physical and chemical indicators:

Physical State

The skin care soap has good stability, characteristic *Zanthoxylum schinifolium* fragrance, and exquisite uniform pale yellow color, and is translucent.

pH Value

Take the skin care soaps prepared in Example 1 to Example 4, wet them with distilled water, and test them with pH papers. The pH values range between 7.5-10.0.

Skin Irritation and Allergic Reaction Tests

Take 12 experimental mice, remove the hair on the back of each mouse by rosin hot-melt method, apply the soaps prepared in Example 1 to Example 4 that have wetted by distilled water to the bare skin, observe 1 hour after the application, and compare the treated skin with untreated skin. The results showed the skin care soaps did not cause irritation or allergic reaction.

Apply the skin care soaps prepared in Example 1 to Example 4 that have been wetted by distilled water to the back of the hands of volunteers (12-60 years old, 58 volunteers), observe 30 minutes after the application. No skin redness, itching, blistering, or rash were observed.

Experiment 2

Bactericidal and Fungicidal Effects of *Zanthoxylum schinifolium* Skin Care Soaps Prepared in Example 1 to Example 4

Materials and Method

Material

Test sample: *Zanthoxylum schinifolium* skin care soap prepared in Example 1 to Example 4.

Test strain: Fungi: *Candida albicans C. albicans* (SC5314). Bacteria: *Pseudomonas aeruginosa*(PA14).

Medium: yeast extract peptone glucose (YPD) agar medium.

Preparation of bacterium and fungus suspensions: bacterial or fungal suspension was prepared by agar plate method, and the test bacterium or fungus was activated on the slant medium for two generations. Then, the bacterium or fungus rings were scraped from the slant surface with tweezers, and were collected in triangular flasks containing different volumes of sterile physiological saline, respectively. The suspension of *Candida albicans* was prepared with the final concentration of $1\times10^4$ CFU/mL, and the suspension of *Pseudomonas aeruginosa* was prepared with the final concentration of $1\times10^8$ CFU/mL.

Determination of Bactericidal and Fungicidal Activity

Mix the soap samples and bacterium or fungus suspension in a 96-well plate, set aside for 1 minute, draw 10 μL suspension, drop on the YPD solid medium, and culture for 24 hours, count the number of colonies and repeat three times.

The results of fungicidal activity against the *Candida albicans* of *Zanthoxylum schinifolium* skin care soaps prepared in Example 1 to Example 4 are shown in Table 1, Table 2, Table 3 and Table 4, respectively; and the results of bactericidal activity against *Pseudomonas aeruginosa* of the *Zanthoxylum schinifolium* skin care soaps prepared in Example 1 to Example 4 are shown in Table 5, Table 6, Table 7 and Table 8, respectively.

The results of the fungicidal test on *Candida albicans* by the *Zanthoxylum schinifolium* skin care soap prepared in Example 1 for 1 minute are shown in Table 1; the results of fungicidal test on *Candida albicans* by the *Zanthoxylum schinifolium* skin care soap prepared in Example 2 for 1 minute are shown in Table 2; the results of fungicidal test on *Candida albicans* by the *Zanthoxylum schinifolium* skin care soap prepared in Example 3 for 1 minute are shown in Table 3; and the results of fungicidal test on *Candida albicans* by the *Zanthoxylum schinifolium* skin care soap prepared in Example 4 for 1 minute are shown in Table 4. The results of the bactericidal test on *Pseudomonas aeruginosa* by the *Zanthoxylum schinifolium* skin care soap prepared in Example 1 for 1 minute are shown in Table 5; the results of bactericidal test on *Pseudomonas aeruginosa* by the *Zanthoxylum schinifolium* skin care soap prepared in Example 2 for 1 minute are shown in Table 6; the results of bactericidal test on *Pseudomonas aeruginosa* by the *Zanthoxylum schinifolium* skin care soap prepared in Example 3 for 1 minute are shown in Table 7; and the results of bactericidal test on *Pseudomonas aeruginosa* by the *Zanthoxylum schinifolium* skin care soap prepared in Example 4 for 1 minute are shown in Table 8.

TABLE 1

| | Sample Dilution Factor | | | | | |
|---|---|---|---|---|---|---|
| | ½ | ¼ | ⅛ | 1/16 | 1/32 | 1/64 |
| Repeat 1 | 0 | >20 | >20 | >20 | >20 | >20 |
| Repeat 2 | 0 | >20 | >20 | >20 | >20 | >20 |
| Repeat 3 | 0 | >20 | >20 | >20 | >20 | >20 |

TABLE 2

| | Sample Dilution Factor | | | | | |
|---|---|---|---|---|---|---|
| | ½ | ¼ | ⅛ | 1/16 | 1/32 | 1/64 |
| Repeat 1 | 0 | >20 | >20 | >20 | >20 | >20 |
| Repeat 2 | 0 | >20 | >20 | >20 | >20 | >20 |
| Repeat 3 | 0 | >20 | >20 | >20 | >20 | >20 |

TABLE 3

| | Sample Dilution Factor | | | | | |
|---|---|---|---|---|---|---|
| | ½ | ¼ | ⅛ | 1/16 | 1/32 | 1/64 |
| Repeat 1 | 0 | >20 | >20 | >20 | >20 | >20 |
| Repeat 2 | 0 | >20 | >20 | >20 | >20 | >20 |
| Repeat 3 | 0 | >20 | >20 | >20 | >20 | >20 |

TABLE 4

| | Sample Dilution Factor | | | | | |
|---|---|---|---|---|---|---|
| | ½ | ¼ | ⅛ | 1/16 | 1/32 | 1/64 |
| Repeat 1 | 0 | >20 | >20 | >20 | >20 | >20 |
| Repeat 2 | 0 | >20 | >20 | >20 | >20 | >20 |
| Repeat 3 | 0 | >20 | >20 | >20 | >20 | >20 |

TABLE 5

| | Sample Dilution Factor | | | | | |
|---|---|---|---|---|---|---|
| | ½ | ¼ | ⅛ | 1/16 | 1/32 | 1/64 |
| Repeat 1 | 0 | 12 | >20 | >20 | >20 | >20 |
| Repeat 2 | 0 | 9 | >20 | >20 | >20 | >20 |
| Repeat 3 | 0 | 11 | >20 | >20 | >20 | >20 |

TABLE 6

| | Sample Dilution Factor | | | | | |
|---|---|---|---|---|---|---|
| | ½ | ¼ | ⅛ | 1/16 | 1/32 | 1/64 |
| Repeat 1 | 0 | 11 | >20 | >20 | >20 | >20 |
| Repeat 2 | 0 | 7 | >20 | >20 | >20 | >20 |
| Repeat 3 | 0 | 15 | >20 | >20 | >20 | >20 |

TABLE 7

| | Sample Dilution Factor | | | | | |
|---|---|---|---|---|---|---|
| | ½ | ¼ | ⅛ | 1/16 | 1/32 | 1/64 |
| Repeat 1 | 0 | 8 | >20 | >20 | >20 | >20 |
| Repeat 2 | 0 | 8 | >20 | >20 | >20 | >20 |
| Repeat 3 | 0 | 12 | >20 | >20 | >20 | >20 |

TABLE 8

| | Sample Dilution Factor | | | | | |
|---|---|---|---|---|---|---|
| | ½ | ¼ | ⅛ | 1/16 | 1/32 | 1/64 |
| Repeat 1 | 0 | 10 | >20 | >20 | >20 | >20 |
| Repeat 2 | 0 | 12 | >20 | >20 | >20 | >20 |
| Repeat 3 | 0 | 9 | >20 | >20 | >20 | >20 |

This experiment selected *Candida albicans* as a representative fungus that is harmful to the human body, and *Pseudomonas aeruginosa* as a representative bacterium that is harmful to the human body. The rapid killing effect of the *Zanthoxylum schinifolium* skin care soap prepared in Example 1 to Example 4 on these two pathogens was examined.

The results showed that the *Zanthoxylum schinifolium* skin care soaps prepared in Example 1 to Example 4 had prominent killing effect on *Candida albicans* and *Pseudomonas aeruginosa*, and the sterilization rate reached 100% in 1 minute, and the soaps had very excellent bactericidal and fungicidal effect.

Experiment 3

Evaluation of the Effectiveness of the *Zanthoxylum schinifolium* Skin Care Soaps

*Zanthoxylum schinifolium* skin care soaps prepared in Example 1 to Example 4 were evaluated using consumer surveys. 56 subjects aged 18-55 years old were selected as trial subjects, and were randomly divided into 4 trial groups. The *Zanthoxylum schinifolium* skin care soaps prepared in Example 1 to Example 4 were tried in each group. The usage requirements were three times a day for the morning, evening and evening cleansing for 6 weeks. The highest score was 10: 10 points means very satisfactory and very effective; 8 points means satisfactory and effective; 6 points means acceptable and generally effective; and less than 6 points means unacceptable and not effective. The tabulated effects of the *Zanthoxylum schinifolium* skin care soaps, in average score, are shown in Table 9:

TABLE 9

| Effectiveness | Example 1 Average score | Example 2 Average score | Example 3 Average score | Example 4 Average score | Tabulated score |
|---|---|---|---|---|---|
| Cleansing Capacity | 10 | 10 | 10 | 10 | 10 |
| Foaming Ability | 9.8 | 9.9 | 9.7 | 9.5 | 9.7 |
| Moisturizing Ability | 9.2 | 9.4 | 9.4 | 9.3 | 9.3 |
| Nourishing Ability | 8.8 | 9.0 | 9.2 | 9.1 | 9.0 |

As shown in Table 9, the bactericidal, fungicidal and anti-allergenic *Zanthoxylum schinifolium* skin care soaps of the present invention have a high foaming ability, have a high cleaning capacity, have an excellent ability of moisturizing and nourishing skin, and also have an excellent bactericidal and fungicidal effect.

The basic principles, principal features and advantages of the present invention have been shown and described. It should be understood by those skilled in the art that the present invention is not limited to the embodiments described above and that the foregoing embodiments and description are intended to be illustrative of the principles of the invention. Various changes and modifications may be made without departing from the spirit and scope of the invention as defined by the appended claims, the description and the equivalents thereof.

What is claimed is:

1. A bactericidal, fungicidal and anti-allergenic *Zanthoxylum schinifolium* skin care soap comprising based on weight percentage:

| | | |
|---|---|---|
| Component A: | *Zanthoxylum schinifolium* nut oil | 15.0-21.0%, |
| | Propylene glycol | 12.0-17.0%, |
| | Glycerin | 6.0-11.0%; |
| Component B: | Deionized water | 5.0-8.0%, |
| | Sodium alkyl ether sulfate AES | 8.0-12.0%; |
| Component C: | Lauric acid | 5.0-8.0%, |
| | Stearic acid | 11.0-16.0%; |
| Component D: | 98% NaOH | 2.5-4.5%, |
| | Deionized water | balance; and |
| Component E: | *Zanthoxylum schinifolium* essential oil | 0.3-2%. |

2. A bactericidal, fungicidal and anti-allergenic *Zanthoxylum schinifolium* skin care soap comprising based on weight percentage:

| | | |
|---|---|---|
| Component A: | *Zanthoxylum schinifolium* nut oil | 16.0-20.0%, |
| | Propylene glycol | 13.0-16.0%, |
| | Glycerin | 7.0-10.0%; |

-continued

| | | |
|---|---|---|
| Component B: | Deionized water | 6.0-8.0%, |
| | Sodium alkyl ether sulfate AES | 9.0-12.0%; |
| Component C: | Lauric acid | 6.0-8.0%, |
| | Stearic acid | 12.0-15.0%; |
| Component D: | 98% NaOH | 2.5-4.0%, |
| | Deionized water | balance; and |
| Component E: | *Zanthoxylum schinifolium* essential oil | 0.3-2%. |

3. The bactericidal, fungicidal and anti-allergenic *Zanthoxylum schinifolium* skin care soap of claim 1 comprising based on weight percentage:

| | | |
|---|---|---|
| Component A: | *Zanthoxylum schinifolium* nut oil | 15.0-21.0%, |
| | Propylene glycol | 12.0-17.0%, |
| | Glycerin | 6.0-11.0%; |
| Component B: | Deionized water | 5.0-8.0%, |
| | Sodium alkyl ether sulfate AES | 8.0-12.0%; |
| Component C: | Lauric acid | 5.0-8.0%, |
| | Stearic acid | 11.0-16.0%; |
| Component D: | 98% NaOH | 2.5-4.5%, |
| | Deionized water | balance; and |
| Component E: | *Zanthoxylum schinifolium* essential oil | 0.3-0.8%. |

4. The bactericidal, fungicidal and anti-allergenic *Zanthoxylum schinifolium* skin care soap of claim 2 comprising based on weight percentage:

| | | |
|---|---|---|
| Component A: | *Zanthoxylum schinifolium* nut oil | 16.0-20.0%, |
| | Propylene glycol | 13.0-16.0%, |
| | Glycerin | 7.0-10.0%; |
| Component B: | Deionized water | 6.0-8.0%, |
| | Sodium alkyl ether sulfate AES | 9.0-12.0%; |
| Component C: | Lauric acid | 6.0-8.0%, |
| | Stearic acid | 12.0-15.0%; |
| Component D: | 98% NaOH | 2.5-4.0%, |
| | Deionized water | balance; and |
| Component E: | *Zanthoxylum schinifolium* essential oil | 0.3-0.6%. |

5. The *Zanthoxylum schinifolium* skin care soap of claim 1, comprising:

Component A: *Zanthoxylum schinifolium* nut oil 18 wt %, Propylene glycol 13.0 wt %-16.0 wt %, Glycerin 7.0 wt %-10.0 wt %;

Component B: Deionized water 6.0 wt %-8.0 wt %, Sodium alkyl ether sulfate AES 9.0 wt-12.0 wt %;

Component C: Lauric acid 6.0 wt %-8.0 wt %, Stearic acid 12.0 wt %-15.0 wt %;

Component D: 98% NaOH 2.5 wt %-4.0 wt %, Deionized water balance; and

Component E: *Zanthoxylum schinifolium* essential oil 2 wt %, wherein the skincare soap is bactericidal, fungicidal and anti-allergenic.

* * * * *